US00PP27401P3

(12) United States Plant Patent
Clark et al.

(10) Patent No.: US PP27,401 P3
(45) Date of Patent: Nov. 22, 2016

(54) BLACKBERRY PLANT NAMED 'APF-122'

(50) Latin Name: ***Rubus* subgenus *Rubus* Watson**
Varietal Denomination: APF-122

(71) Applicant: The Board of Trustees of The University of Arkansas, Little Rock, AR (US)

(72) Inventors: John Reuben Clark, Fayetteville, AR (US); Ellen Thompson, Fayetteville, AR (US); Mario Aguas-Alvarado, Salinas, CA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 67 days.

(21) Appl. No.: 13/999,390

(22) Filed: Feb. 20, 2014

(65) Prior Publication Data

US 2015/0237785 P1 Aug. 20, 2015

(51) Int. Cl.
*A01H 5/08* (2006.01)

(52) U.S. Cl.
USPC ..... Plt./203

(58) Field of Classification Search
USPC ..... Plt./203
See application file for complete search history.

*Primary Examiner* — Keith Robinson
(74) *Attorney, Agent, or Firm* — King IP Law; Joshua King

(57) ABSTRACT

A new and distinct cultivar of blackberry plant named 'APF-122'. Characteristics include its precocity, high soluble solids (even at the red-black stage), very little postharvest reddening (<10%), heavy over-crops on its compact primocanes such that a floricane crop would generally not be economically viable.

3 Drawing Sheets

BACKGROUND AND SUMMARY

Blackberries (*Rubus* subgenus *Rubus* Watson) are a well-known, aggregate fruit that are becoming increasingly popular throughout the world. Recent efforts at the University of Arkansas, using traditional breeding techniques and testing selections under mild climate conditions along the western coast of the USA, have led to the development of the world's first primocane-fruiting cultivars. Primocane-fruiting blackberries, in contrast to floricane-fruiting types, provide growers with the ability to produce fruit on first year canes (i.e., primocanes), as well as second-year canes (i.e., floricanes). In addition, primocane-fruiting blackberries produce fruit in late summer to autumn, whereas floricane-fruiting types generally fruit in early to mid-summer. The ability to extend the harvest season offers fresh market growers a significant economic advantage.

One example of an existing primocane-fruiting blackberry variety is 'APF-45' (marketed under the trade name 'PRIME ARK® 45'), U.S. Plant Pat. No. 22,449. Another example of an existing, patent-pending primocane-fruiting blackberry variety is 'Camila', U.S. Plant Pat. No. 26,368. A further example of an existing primocane-fruiting blackberry variety is 'Reuben', U.S. Plant Pat. No. 23,497.

Compared to 'APF-45', the present cultivar, 'APF-122', is different because the fruit size is smaller (5.8 g vs. 8.8 g, on average) and significantly earlier in fruiting season (average ripe fruit date for primocanes on 'APF-122' is 5-6 months after planting vs. 8-9 months after planting 'APF-45').

Compared to 'Camila', the fruit shape of 'Camila' is elongated, while the fruit shape of 'APF-122' is round. Fruits of 'Camila' have only moderate firmness, while 'APF-122' is very firm.

Compared to 'Reuben', the fruits of 'Reuben' are much larger than 'APF-122', averaging 14.5 g versus 5.8 g, respectively. Also, 'Reuben' is a late-fruiting variety, while 'APF-122' is considered early for a primocane-fruiting type. The fruits of 'Reuben' are oblong and blocky, while fruits of 'APF-122' are round.

Distinctive characteristics of 'APF-122' include its precocity, high soluble solids (even at the red-black stage) and very little postharvest reddening (<10%). 'APF-122' is also unique in that it over-crops so heavily on its compact primocanes that a floricane crop would generally not be economically viable. Normally in commercial practice, primocane-fruiting blackberries are pinch pruned (i.e., the tips are pinched out at the appropriate stage of growth) in order to force more fruiting laterals. However, in the case of 'APF-122', given its high yield potential and precocity, it may prove that in commercial practice that the need for such pinching may be reduced or even eliminated.

BRIEF DESCRIPTION OF THE PHOTOGRAPHS

DETAILED DESCRIPTION

Figure 1:
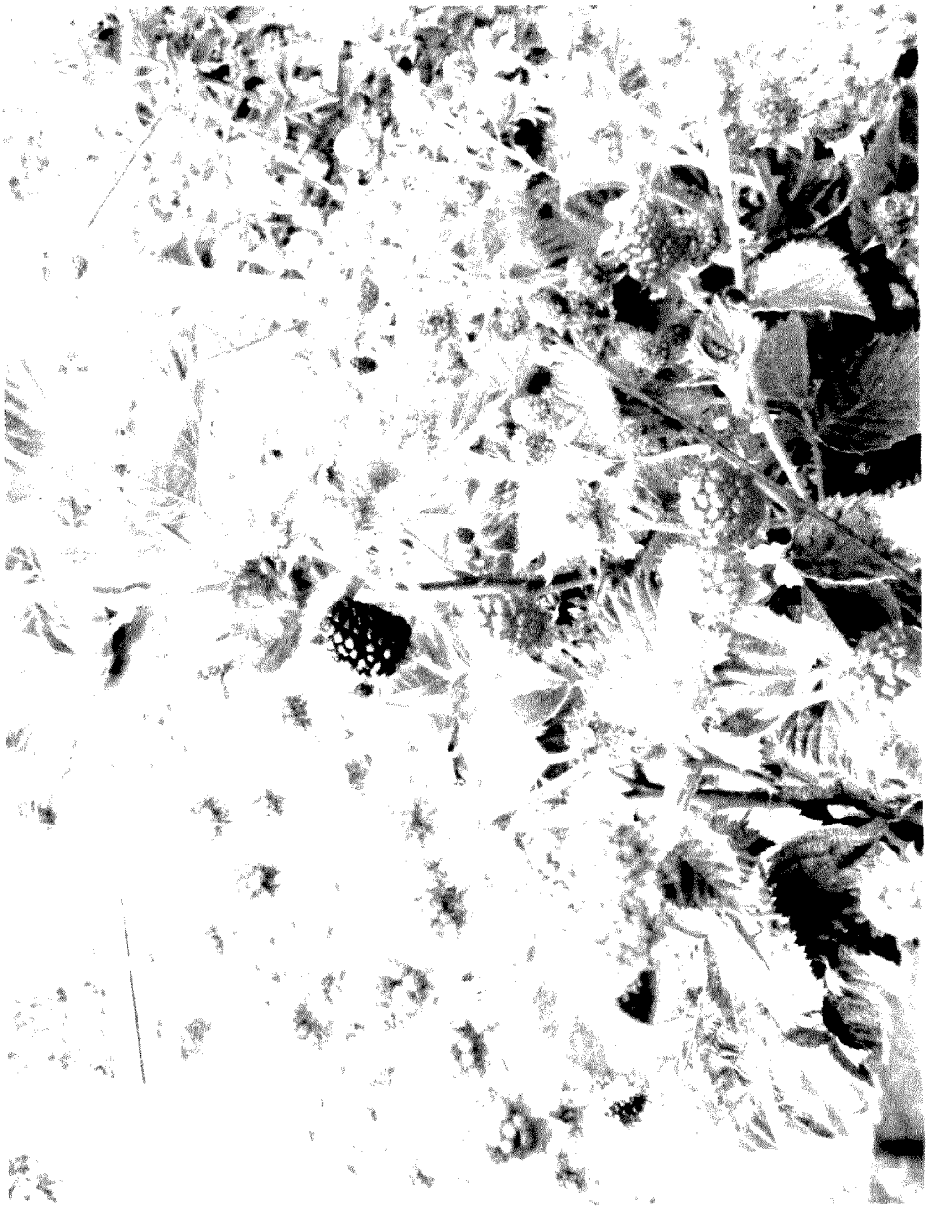
FIG. 1 is a photograph showing fruit of the Blackberry cultivar 'APF-122' at the ripening stage, along with crop load on one-year old canes. The photo was taken of plants having a crown aged of 1 year and cane age of 8 months.
Figure 2:
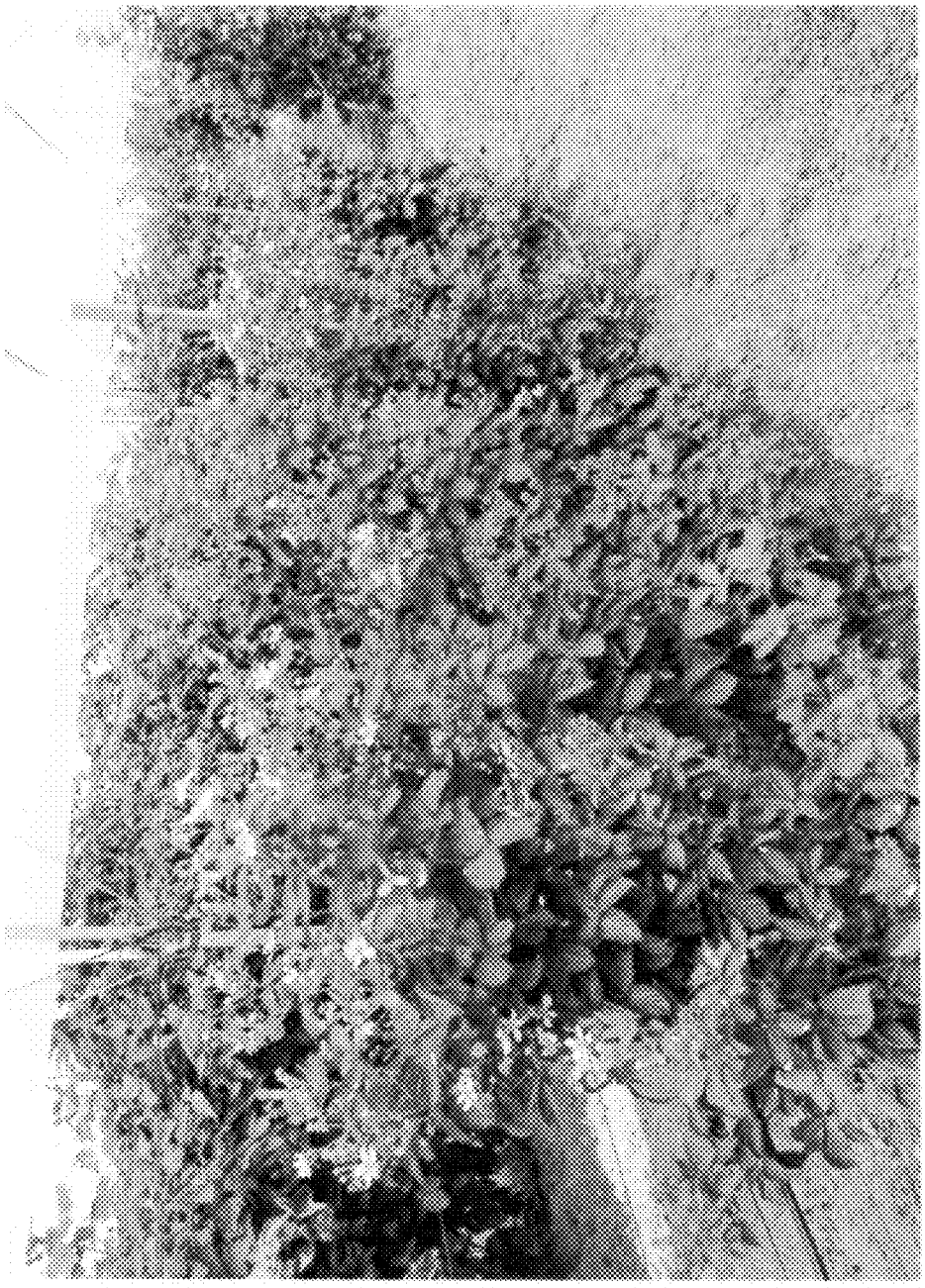
FIG. 2 is a photograph showing the full plant the Blackberry cultivar 'APF-122' at the flowering stage. The photo was taken of plants having a crown aged of 3 years and cane age of 8 months.
Figure 3:
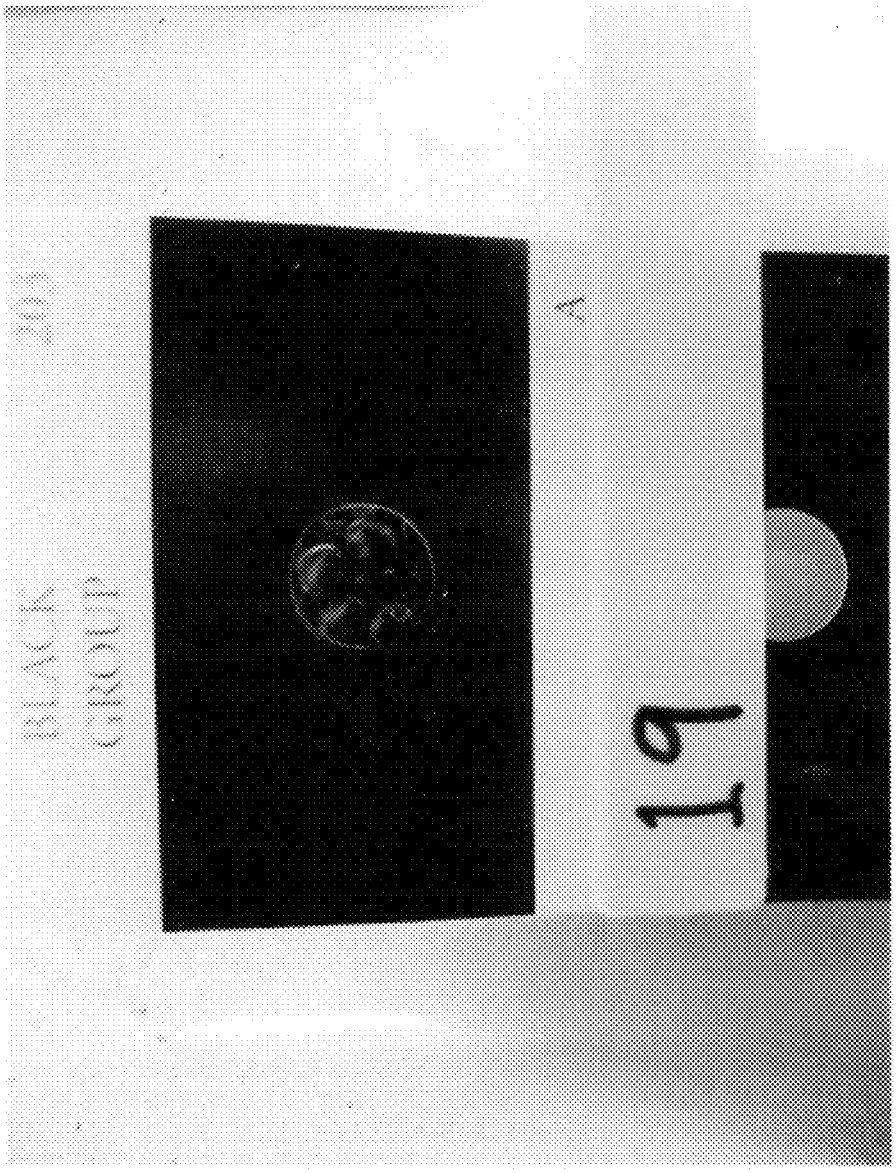
FIG. 3 is a photograph showing an exemplary fruit of the Blackberry cultivar 'APF-122' exhibiting color in accord with Royal Horticultural Society's (RHS) Black Group 203A. The photo was taken of fruit from plants having a crown aged of 3 years.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are from specimen plants with a crown age of 1 year and a cane age of 8 months that were observed in summer 2013 in Watsonville, Calif. The color determination is in accordance with The 2007 R.H.S. Colour Chart (Fifth Edition) of The Royal Horticultural Society, London, England, except where general color terms of ordinary dictionary significance are used.

Cultivar name: 'APF-122'.

Classification:

*Family*.—Rosaceae.

*Botanical name*.—*Rubus* Subgenus *Rubus* Watson.

*Common name*.—Blackberry.

Parentage:

*Female parent*.—Name: 'APF-45', U.S. Plant Pat. No. 22,449. Compared to 'APF-45', the present cultivar, 'APF-122', is different because the fruit size is smaller (5.8 g vs. 8.8 g, on average) and significantly earlier in fruiting season (average ripe fruit date for primocanes is 5-6 months after planting vs. 8-9 months after planting 'APF- 45').

*Male parent*.—Name: 'A-2286'. This was a proprietary breeding line that was never patented. This line has been discarded due to winter injury susceptibility. 'A-2286' is thorny genotype with thornless alleles. 'A-2286' is larger than 'APF-122', has taller canes, and was later ripening as well as fruited only on floricanes.xxx The new and distinct cultivar of blackberry originated from a hand-pollinated cross of Arkansas selections 'APF-45'×'A-2286' (non-patented, unreleased genotype; male) made in 2003 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the winter to early spring of 2004 and planted in a field near Clarksville, Ark. The seedlings fruited in the summer of 2005 on floricanes and one seedling, designated 'APF-122', was selected in 2005 for its firmness and low-acid flavor, good crop potential, early primocane bloom and plant health.

During late summer of 2005 the original plant selection was propagated asexually from root cuttings at the above-noted location, and a test row of 20 plants was established. Subsequently, larger test plantings have been established with asexually multiplied plants at Clarksville, Ark. and Watsonville, Calif.

The new cultivar has been asexually multiplied annually since 2006 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

General description: Plants of 'APF-122' have moderate vigor, but are highly precocious. Actively growing canes tend to shift from vegetative to reproductive state at approx. 0.75 m in height and do not require pinching. Canes are erect in growth habit, even in Year 1, and are of small to medium stature. 'APF-122' can be considered to have a vase form/shape with a growth habit of erect canes. The height averages 1.1 m as measured from cane base to cane apex. The spread is 33 cm as measured from leaf tip to leaf tip. The time to initiate and develop roots from adventitious shoots is 30 days. Root growth in spring and summer is fibrous and spreading to the width of the aerial canopy, generally with a 75:25 ratio of brown lignified coarse roots and off-white fine (feeder) roots, respectively.

*Growth*.—Plants of 'APF-122' have moderate vegetative vigor and erect growth habit. Primocanes emerge both from the crown of the plant as well as from the roots (as suckers).

*Growth rate*.—The growth rate of 'APF-122' is moderate, with canes reaching 1.2 meters in height within five (5) months of emergence.

*Productivity*.—Moderate (see fruit yield). 'APF-122' is considered to be economically viable under comercial production systems in California, USA.

*Cold hardiness*.—Unknown.

*Branching height of the plants*.—Natural branching occurs, but is variable. Typically, starting at about 0.5 to 0.75 m in height, fruiting laterals begin to elongate at nearly every node.

Canes: The following discussion is directed to primocanes; floricane data is omitted because this cultivar is strongly primocane-fruiting.

*General description*.—Thorny, erect.

| | | Base | Middle | Tip |
|---|---|---|---|---|
| Diameter: | | 0.9 cm | 0.8 cm | 0.3 cm |
| Length: | 1.1 m | | | |
| Number of Nodes: | 31 | | | |
| Internode length: | | 3.6 cm | 2.8 cm | 1.8 cm |
| Number of canes/hill: | 4-6 | | | |
| Cane Color: | RHS 143A | | | |
| Predominant branch distribution: | Only on upper half. | | | |
| Spines (present or absent): | Present | | | |
| Density: | | $3/cm^2$ | $3/cm^2$ | $2/cm^2$ |
| Shape: | Acute | | | |
| Length: | 0.9 cm | | | |
| Width: | | 0.2 cm | 0.1 cm | 0.05 cm |
| Apex descriptor: | Lanceolate | | | |
| Color: | Base = RHS N144D Tip = RHS 166B | | | |
| Texture: | Glabrous | | | |
| Attitude: | Upwards | | | |

*Bud shape*.—Acute. Length: 0.9 cm. Diameter (base): 0.3 cm. Diameter (tip): 0.1 cm. Color: RHS 195A. Texture: Pubescent.

Foliage:

*General description*.—Leaves during vegetative growth are pentafoliate, while leaves which develop on fruiting laterals are trifoliate. All leaves have abaxial trichomes, soft to the touch. The adaxial surface of the leaves have fewer trichomes and are rugose to the touch. The leaflets are triply serrate. There are small spines on the under-part of the leaf rib. The petioles and petiolules often have a deep red hue under full sun conditions, yet tend not to develop the pigment (i.e., remain green) under high tunnels covered with plastic film, which diffuses light. It is common for petioles to partially develop pigmentation, often only at the distal and basal portion. High tunnels placed over blackberry plants in California during bloom is considered standard practice. Plants of 'APF-122' used in this description were observed while under high tunnels.

Leaves:

*Complete leaf.*—Length: 19.2 cm. Width: 17.4 cm. Number of leaflets: 5.

*Terminal leaflet.*—Size. Length (cm): 8.3 cm. Width (cm): 7.1 cm. Length/Width ratio: 1.17. Shape of apex: Acuminate. Shape of Base base: Cordate. Margin: Triple serrate. Upper leaf texture: Smooth with mild interveinal puckering. Lower leaf texture: Pubescent. Number of serrations/leaf 139. Shape of serrations: Flexuous — Flexuous. Color. Upper surface: RHS 147A. Lower surface: RHS 138A. Venation pattern: Alternately Pinnate. Venation Color: Upper surface: RHS 146D. Lower surface: RHS N144D. Leaf pubescence density: Moderate. Color of leaf pubescence: RHS 157D. Shape of leaf in cross-section: Simple Cordate Leaflet. Number of leaflets/leaf: 5. Interveinal blistering: Moderate. Glossiness: Moderate (upper leaf surface only).

*Primocane leaves.*—Petiole length: 7.3 cm. Petiole diameter: 0.2 cm. Petiole color. Upper: RHS 143A under diffuse light conditions (i.e., under a high tunnel covered with plastic film). RHS 183B (under full sun conditions). Lower: RHS 144B. Petiole texture: Pubescent. Petiolie strength: High (does not detach easily, even in dormancy). Rachis length: 3.7 cm. Rachis color: RHS 143A. Rachis texture: Pubescent. Stipule length: 1.6 cm. Stipules per leaf: 2. Stipule width: 1.6 cm. Stipule color: Accent — RHS 165A Undertone — RHS 143A. Upper surface: RHS 147A. Lower surface: RHS 138A. Stipule texture: Pubescent.

*Terminal leaflet.*—Length: 8.3 cm. Width: 6.7 cm. Rachis length: 3.7 cm.

*Distal lateral leaflet.*—Length: 7.85 cm. Width: 6.15 cm. Petiolule length: 1.8 cm. Petiolule color: RHS 143A. Petiolule texture: Pubescent. Petiolule strength: High.

*Basal lateral leaflet.*—Length: 7.0 cm. Width: 5.2 cm. Petiolule length: 0.5 cm.

Flowers:

*Time of flowering* (50% *of plants at first flower*).—June 15 on primocanes.

*Size.*—Length: 1.3 cm. Diameter: 4.3 cm.

*Fragrance.*—None.

*Peduncle.*—Length: 0.1 cm. Diameter: 0.6 cm. Color: RHS 141C. Pubescence: RHS 157D. Texture: Smooth with few undulations. Strength: Very high.

*Perianth.*—Flowering trusses shape: Truncate.

*Petals.*—Color (upper and lower): RHS NN155B. Number per flower: 5. Shape: Elliptical. Length: 2.0 cm. Width: 1.3 cm. Apex descriptor: Rounded. Base Descriptor: Truncate. Margin descriptor: Crenate.

*Sepals.*—Quantity: 5. Length: 0.6 cm. Width: Base — 0.5 cm Middle — 0.4 cm Tip — 0.05 cm. Color: RHS 143B. Apex descriptor: Acuminate. Outer texture: Pubescent. Inner texture: Pubescent.

*Margin descriptor.*—Entire.

*Pedicel.*—Color: RHS 144A. Length: 4.7 cm. Diameter: 0.1 cm. Strength: Very high.

*Reproductive organs.*—Self-fertile: Yes.

*Male.*—Stamen Number: 178. Length: 0.5 cm. Diameter: 0.05 cm. Color: RHS NN155D. Anther Length: 0.01 cm. Diameter: 0.01 cm. Color: RHS 199A. Filament length: 0.6 cm. Filament color: RHS 155A.

*Pollen.*—Color: RHS 163D. Amount: moderate.

*Female.*—Style. Length: 0.3 cm. Diameter: 0.05 cm. Color: RHS 149A. Stigma. Length: 0.05 cm. Diameter: 0.05 cm. Color: RHS 149A. Ovary. Color: RHS 144A.

Fruit (the following observations correlate to primocane fruit):

*General description.*—King berries of 'APF-122' are medium-large and round in shape, but sometimes develop a slightly elongated shape. Secondary berries are medium size and always round. Berries are very firm. There is little color change (reversion) in drupelets from black to red in postharvest cold storage and the fruits can be stored for a long time (up to seven days). There is little to no incidence of post-harvest decay or rot (during seven days of storage at 5° C.).

*Predominant shape.*—Round. Weight (g): 5.8 g. Length: 2.8 cm. Width: 2.1 cm. Length/Width ratio: 1.33.

*Receptacle.*—Length: 2.1 cm. Diameter: 0.8 cm. Color: RHS 142C.

*Drupelet.*—Length: 0.6 cm. Diameter: 0.5 cm. Number: 101. Weight: 0.3 g.

*Fruit color.*—External: RHS 203A.

*Internal.*—N/A.

*Firmness of skin.*—Very Firm.

*Firmness of flesh.*—Very Firm.

*Hollow center.*—Absent.

*Number of fruit per node.*—5.3.

*Time of ripening* (50% *of plants with first fruit*).—August 1 on first-year primocanes.

*Time of fruiting.*—August-October.

*Type of bearing.*—Primocane only.

*Fruit yield.*—12,500-14,000 lb/a.

*Average brix.*—11.1.

*Acidity.*—4 (scored on a scale of 1 to 5, where 1=extremely acid, and 5=no acids detectable. Sensory scoring was done on fruit that was cold stored at 1.1° C. for 7 days, and then allowed to warm to room temperature. Titrateable acidity was not measured).

*Market use.*—Fresh.

*Keeping quality.*—Excellent.

*Shipping quality.*—Excellent.

Pest and disease resistance: Trials have shown high field tolerance to powdery mildew (*Podosphaera aphanis*), anthracnose (*Elisinoe veneta*), crown gall (*Agrobacterium tumefaciens*), and botrytis (*Botrytis cinerea*).

What is claimed is:

1. A new and distinct cultivar of blackberry plant named 'APF-122' as described and shown herein.

* * * * *